US012600942B2

(12) United States Patent
Butovsky et al.

(10) Patent No.: US 12,600,942 B2
(45) Date of Patent: Apr. 14, 2026

(54) REPROGRAMMING CELLS INTO HOMEOSTATIC MICROGLIA

(71) Applicants: The Brigham and Women's Hospital, Inc., Boston, MA (US); University of Massachusetts, Boston, MA (US); Massachusetts Institute of Technology, Cambridge, MA (US)

(72) Inventors: Oleg Butovsky, Boston, MA (US); Vladimir Litvak, Holden, MA (US); William Ralvenius, Somerville, MA (US); Li-Huei Tsai, Cambridge, MA (US)

(73) Assignees: The Brigham and Women's Hospital, Inc., Boston, MA (US); Massachusetts Institute of Technology, Cambridge, MA (US); University of Massachusetts, Westborough, MA (US)

( * ) Notice: Subject to any disclaimer, the term of this patent is extended or adjusted under 35 U.S.C. 154(b) by 818 days.

(21) Appl. No.: 17/778,270

(22) PCT Filed: Nov. 20, 2020

(86) PCT No.: PCT/US2020/061637
§ 371 (c)(1),
(2) Date: May 19, 2022

(87) PCT Pub. No.: WO2021/102347
PCT Pub. Date: May 27, 2021

(65) Prior Publication Data
US 2022/0411751 A1      Dec. 29, 2022

Related U.S. Application Data

(60) Provisional application No. 62/938,113, filed on Nov. 20, 2019.

(51) Int. Cl.
*C12N 5/079*      (2010.01)
*A61K 35/30*      (2015.01)

(52) U.S. Cl.
CPC ............ *C12N 5/0622* (2013.01); *A61K 35/30* (2013.01); *C12N 2501/15* (2013.01); *C12N 2501/24* (2013.01); *C12N 2506/115* (2013.01)

(58) Field of Classification Search
None
See application file for complete search history.

(56) References Cited

U.S. PATENT DOCUMENTS

2017/0253856 A1 * 9/2017 Douvaras ................ A61P 25/00

FOREIGN PATENT DOCUMENTS

WO      WO 2018/200669      11/2018

OTHER PUBLICATIONS

Baust, et al. Best practices for cryopreserving, thawing, recovering, and assessing cells. In Vitro Cellular & Developmental Biology—Animal. 53(2017):855-871. Nov. 2, 2017. (Year: 2017).*
Milenkovic, et al. CRISPR-Cas9 mediated TSPO gene knockout alters respiration and cellular metabolism in human primary microglia cells. 20(2019):3359. Jul. 9, 2019. (Year: 2019).*
Etemad, et al. A novel in vitro human microglia model: characterization of human monocyte-derived microglia. Journal of Neuroscience Methods. 2012; 209:79-89. (Year: 2012).*
Butovsky, et al. Identification of a unique TGF-b-dependent molecular and functional signature in microglia. Nature Neuroscience. 2014; 17(4):131-43. (Year: 2014).*
Krasemann, et al. The TREM2-APOE pathway drives the transcriptional phenotype of dysfunctional microglia in neurodegenerative diseases. 2017; 47(3):566-81. (Year: 2017).*
Clanchy, et al. Detection and properties of the human proliferative monocyte subpopulation. 2006; 79:757-66. (Year: 2006).*
Kapellos, et al. Human monocyte subsets and phenotypes in major chronic inflammatory diseases. Frontiers in Immunology. 2019; 10:1-13. (Year: 2019).*
Abud et al., "iPSC-derived human microglia-like cells to study neurological diseases," Neuron, Apr. 19, 2017, 94(2):278, 26 pages.
Ajami et al., "Infiltrating monocytes trigger EAE progression, but do not contribute to the resident microglia pool," Nature Neuroscience, Sep. 2011, 14(9):1142-9.
Ajami et al., "Local self-renewal can sustain CNS microglia maintenance and function throughout adult life," Nature Neuroscience, Dec. 2007, 10(12):1538-43.
Ajami et al., "Single-cell mass cytometry reveals distinct populations of brain myeloid cells in mouse neuroinflammation and neurodegeneration models," Nature Neuroscience, Apr. 2018, 21(4):541-51.
Bai et al., "Microglia and microglia-like cell differentiated from DC inhibit CD4 T cell proliferation," PloS one, Nov. 17, 2009, 4(11):e7869, 9 pages.
Baufeld et al., "Differential contribution of microglia and monocytes in neurodegenerative diseases," Journal of Neural Transmission, May 2018, 125(5):809-26.

(Continued)

*Primary Examiner* — Allison M Fox
*Assistant Examiner* — Gina Pronzati
(74) *Attorney, Agent, or Firm* — Fish & Richardson P.C.

(57) ABSTRACT

Provided herein are methods for obtaining populations of reprogrammed M0-homeostatic tolerogenic microglial cells. The methods include providing an initial population of monocytes, e.g., peripheral blood monocytes (PBMC), from a subject, and reprogramming the cells by maintaining the PBMC in culture ex vivo in the presence of a sufficient amount of transforming growth factor-beta (TGFβ) and interferon-gamma (IFNγ) for a time and under conditions sufficient for the cells to become M0-homeostatic tolerogenic microglia. Also provided are methods of use of these cells, e.g., for the treatment of neurodegenerative diseases associated with inflammation, e.g., Alzheimer's Disease (AD); Multiple Sclerosis (MS), e.g., progressive MS; and Amyotrophic Lateral Sclerosis (ALS).

15 Claims, 9 Drawing Sheets

(56)                  References Cited

OTHER PUBLICATIONS

Baxter et al., "The origin and application of experimental autoimmune encephalomyelitis," Nature Reviews Immunology, Nov. 2007, 7(11):904-12.

Bennett et al., "A combination of ontogeny and CNS environment establishes microglial identity," Neuron, Jun. 27, 2018, 98(6):1170-83.

Bruttger et al., "Genetic cell ablation reveals clusters of local self-renewing microglia in the mammalian central nervous system," Immunity, Jul. 21, 2015, 43(1):92-106.

Butovsky et al., "Microglial signatures and their role in health and disease," Nature Reviews Neuroscience, Oct. 2018, 19(10):622-35.

Butovsky et al., Targeting mi R-155 restores abnormal microglia and attenuates disease in SOD 1 mice. Annals of Neurology, Jan. 2015, 77(1):75-99.

Butovsky et al., "Identification of a unique TGF-β-dependent molecular and functional signature in microglia," Nature Neuroscience, Jan. 2014, 17(1):131-43.

Butovsky et al., "Modulating inflammatory monocytes with a unique microRNA gene signature ameliorates murine ALS," The Journal of Clinical Investigation, Sep. 4, 2012, 122(9):3063-87.

Castellano et al., "Human apoE isoforms differentially regulate brain amyloid-β peptide clearance," Science Translational Medicine, Jun. 29, 2011, 3(89):89ra57.

Cocco et al., "HLA-DR, DQ and APOE genotypes and gender influence in Sardinian primary progressive MS," Neurology, Feb. 8, 2005, 64(3):564-6.

Colonna et al., "Microglia function in the central nervous system during health and neurodegeneration," Annual Review of Immunology, Apr. 4, 2017, 35:441-68.

Carecchio et al., "Microglia function in the central nervous system during health and neurodegeneration," Annual Review of Immunology, Apr. 4, 2017, 35:441-68.

Cronk et al., "Peripherally derived macrophages can engraft the brain independent of irradiation and maintain an identity distinct from microglia," Journal of Experimental Medicine, Jun. 4, 2018, 215(6):1627-47.

Croxford et al., "The cytokine GM-CSF drives the inflammatory signature of CCR2+ monocytes and licenses autoimmunity," Immunity, Sep. 15, 2015, 43(3):502-14.

Etemad et al., "A novel in vitro human microglia model: characterization of human monocyte-derived microglia," Journal of Neuroscience Methods, Jul. 30, 2012, 209(1):79, 12 pages.

Ferber et al., "Mice with a disrupted IFN-gamma gene are susceptible to the induction of experimental autoimmune encephalomyelitis (EAE)," The Journal of Immunology, Jan. 1, 1996, 156(1):5-7.

Gosselin et al., "Environment drives selection and function of enhancers controlling tissue-specific macrophage identities," Cell, Dec. 4, 2014, 159(6):1327-40.

Hammond et al., "Single-cell RNA sequencing of microglia throughout the mouse lifespan and in the injured brain reveals complex cell-state changes," Immunity, Jan. 15, 2019, 50(1):253-71.

Holtzman et al., "Apolipoprotein E and apolipoprotein E receptors: normal biology and roles in Alzheimer disease," Cold Spring Harbor Perspectives in Medicine, Mar. 1, 2012, 2(3):a006312, 24 pages.

Huang et al., "Multiple sclerosis: Pathology, diagnosis and treatments," Experimental and Therapeutic Medicine, Jun. 1, 2017, 13(6):3163-6.

Jack et al., "Microglia and multiple sclerosis," Journal of Neuroscience Research, Aug. 1, 2005, 81(3):363-73.

Keren-Shaul et al., "A unique microglia type associated with restricting development of Alzheimer's disease," Cell, Jun. 15, 2017, 169(7):1276-90.

Kierdorf et al., "Microglia emerge from erythromyeloid precursors via Pu. 1- and Irf8-dependent pathways," Nature Neuroscience, Mar. 2013, 16(3):273-80.

Krasemann et al., "The TREM2-APOE pathway drives the transcriptional phenotype of dysfunctional microglia in neurodegenerative diseases," Immunity, Sep. 19, 2017, 47(3):566-81.

Kristjansdottir et al., "Interferon regulatory factor 5 (IRF5) gene variants are associated with multiple sclerosis in three distinct populations," Journal of Medical Genetics, Jun. 1, 2008, 45(6):362-9.

Lassmann et al., "Progressive multiple sclerosis: pathology and pathogenesis," Nature Reviews Neurology, Nov. 2012, 8(11):647-56.

Liao et al., "Anti-ApoE antibody given after plaque onset decreases Aβ accumulation and improves brain function in a mouse model of Aβ amyloidosis," Journal of Neuroscience, May 21, 2014, 34(21):7281-92.

Lill et al., "Closing the case of APOE in multiple sclerosis: no association with disease risk in over 29 000 subjects," Journal of Medical Genetics, Sep. 1, 2012, 49(9):558-62.

Lin et al., "Bhlhe40 controls cytokine production by T cells and is essential for pathogenicity in autoimmune neuroinflammation," Nature Communications, Apr. 3, 2014, 5(1):1-3.

Lin et al., "APOE4 causes widespread molecular and cellular alterations associated with Alzheimer's disease phenotypes in human iPSC-derived brain cell types," Neuron, Jun. 27, 2018, 98(6):1141-54.

Loma et al., "Multiple sclerosis: pathogenesis and treatment," Current Neuropharmacology, Sep. 1, 2011, 9(3):409-16.

Losonczi et al., "APOE epsilon status in Hungarian patients with primary progressive multiple sclerosis," Swiss Medical Weekly, Nov. 2010, 140:Paper-w13119, 6 pages.

Lu et al., "Macrophages recruited via CCR2 produce insulin-like growth factor-1 to repair acute skeletal muscle injury," The FASEB Journal, Jan. 2011, 25(1):358-69.

Lucchinetti et al., "Heterogeneity of multiple sclerosis lesions: implications for the pathogenesis of demyelination," Annals of Neurology: Official Journal of the American Neurological Association and the Child Neurology Society, Jun. 2000, 47(6):707-17.

Lund et al., "Fatal demyelinating disease is induced by monocyte-derived macrophages in the absence of TGF-β signaling," Nature Immunology, May 2018, 19(5):1-7.

Fani et al., "Innate immune cells: Monocytes, monocyte-derived macrophages and microglia as therapeutic targets for Alzheimer's disease and multiple sclerosis." Frontiers in Cellular Neuroscience, Jul. 31, 2019, 13:355, 9 pages.

Mancuso et al., "Stem-cell-derived human microglia transplanted in mouse brain to study human disease," Nature Neuroscience, Dec. 2019, 22(12):2111-6.

Masuda et al., "IRF8 is a transcriptional determinant for microglial motility," Purinergic Signalling, Sep. 2014, 10(3):515-21.

Mathys et al., "Temporal tracking of microglia activation in neurodegeneration at single-cell resolution," Cell Reports, Oct. 10, 2017, 21(2):366-80.

Mildner et al., "CCR2+ Ly-6Chi monocytes are crucial for the effector phase of autoimmunity in the central nervous system," Brain, Sep. 1, 2009, 132(9):2487-500.

Mildner et al., "Ly-6G+ CCR2—myeloid cells rather than Ly-6ChighCCR2+ monocytes are required for the control of bacterial infection in the central nervous system," The Journal of Immunology, Aug. 15, 2008, 181(4):2713-22.

Mildner et al., "Microglia in the adult brain arise from Ly-6ChiCCR2+ monocytes only under defined host conditions," Nature Neuroscience, Dec. 2007, 10(12):1544-53.

O'Loughlin et al., "Microglial phenotypes and functions in multiple sclerosis," Cold Spring Harbor Perspectives in Medicine, Feb. 1, 2018, 8(2):a028993, 22 pages.

Olsson et al., "Cytokine-producing cells in experimental autoimmune encephalomyelitis and multiple sclerosis," Neurology. Jun. 1, 1995;45(6 Suppl 6):S11-5.

PCT International Preliminary Report on Patentability in International Appln. No. PCT/US2020/061637, dated May 17, 2022, 7 pages.

PCT International Search Report and Written Opinion in International Appln. No. PCT/US2020/061637, dated Mar. 4, 2021, 9 pages.

(56) References Cited

OTHER PUBLICATIONS

Pimenova et al., "A tale of two genes: microglial Apoe and Trem2," Immunity, Sep. 19, 2017, 47(3):398-400.

Ponomarev et al., "Microglial cell activation and proliferation precedes the onset of CNS autoimmunity," Journal of Neuroscience Research, Aug. 1, 2005, 81(3):374-89.

Prineas et al., "Immunopathology of secondary-progressive multiple sclerosis," Annals of Neurology: Official Journal of the American Neurological Association and the Child Neurology Society, Nov. 2001, 50(5):646-57.

Qin et al., "A milieu molecule for TGF-β required for microglia function in the nervous system," Cell, Jun. 28, 2018, 174(1):156-71.

Sanford, "Fingolimod: a review of its use in relapsing-remitting multiple sclerosis," Drugs, Aug. 2014, 74(12):1411-33.

Shi et al., "ApoE4 markedly exacerbates tau-mediated neurodegeneration in a mouse model of tauopathy," Nature, Sep. 2017, 549(7673):523-7.

Shin et al., "Apolipoprotein E mediation of neuro-inflammation in a murine model of multiple sclerosis," Journal of Neuroimmunology, Jun. 15, 2014, 271(1-2):8-17.

Sospedra et al., "Immunology of multiple sclerosis," Annual Review of Immunology, Apr. 23, 2005, 23:683-747.

Steinman, "The discovery of natalizumab, a potent therapeutic for multiple sclerosis," Journal of Cell Biology, Oct. 2012, 199(3):413-6.

Strachan-Whaley et al., "Interactions between microglia and T cells in multiple sclerosis pathobiology," Journal of Interferon & Cytokine Research, Aug. 1, 2014, 34(8):615-22.

Sun et al., "Defective T cell activation and autoimmune disorder in Stra13-deficient mice," Nature Immunology, Nov. 2001, 2(11):1040-7.

Tang et al., "Association between IRF5 polymorphisms and autoimmune diseases: a meta-analysis," Genetic Molecular Research, Oct. 2014, 13(2):4473-85.

clinicaltrials.org, "T-regulatory Cells in ALS (Tregs in ALS)," Aug. 14, 2019, retrieved Dec. 7, 2022 from URL<clinicaltrials.gov/ct2/show/NCT04055623>, 11 pages.

Verghese et al., "ApoE influences amyloid-β (Aβ) clearance despite minimal apoE/Aβ association in physiological conditions," Proceedings of the National Academy of Sciences, May 7, 2013, 110(19):E1807-16.

Willenborg et al., "IFN-gamma plays a critical down-regulatory role in the induction and effector phase of myelin oligodendrocyte glycoprotein-induced autoimmune encephalomyelitis," The Journal of Immunology, Oct. 15, 1996, 157(8):3223-7.

Wong et al., "Mice deficient in NRROS show abnormal microglial development and neurological disorders," Nature Immunology, Jun. 2017, 18(6):633-41.

Yamasaki et al., "Differential roles of microglia and monocytes in the inflamed central nervous system," Journal of Experimental Medicine, Jul. 28, 2014, 211(8):1533-49.

Yednock et al., "Prevention of experimental autoimmune encephalomyelitis by antibodies against α4β1 integrin," Nature, Mar. 1992, 356(6364):63-6.

Zrzavy et al., "Loss of 'homeostatic' microglia and patterns of their activation in active multiple sclerosis," Brain, Jul. 1, 2017, 140(7):1900-13.

* cited by examiner a
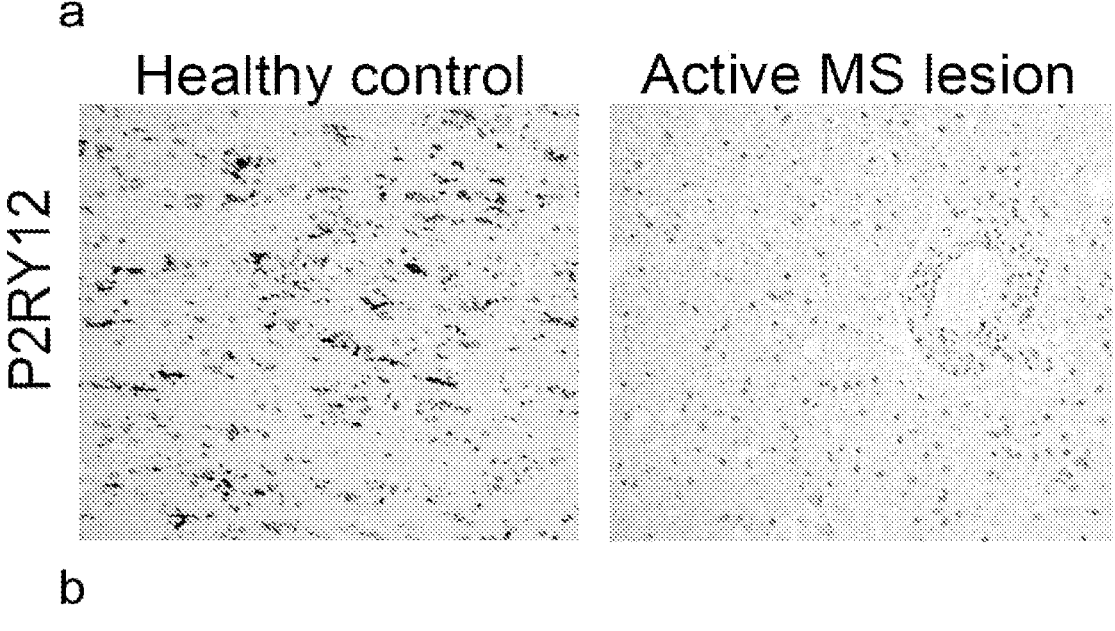
Healthy control        Active MS lesion
P2RY12
b
*APOE* expression
(Intact vs. Lesion)
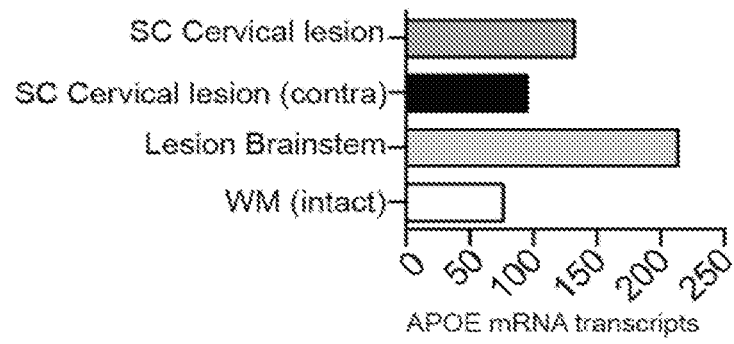
SC Cervical lesion
SC Cervical lesion (contra)
Lesion Brainstem
WM (intact)
0    50    100    150    200    250
APOE mRNA transcripts
*FIGs. 3A-B*

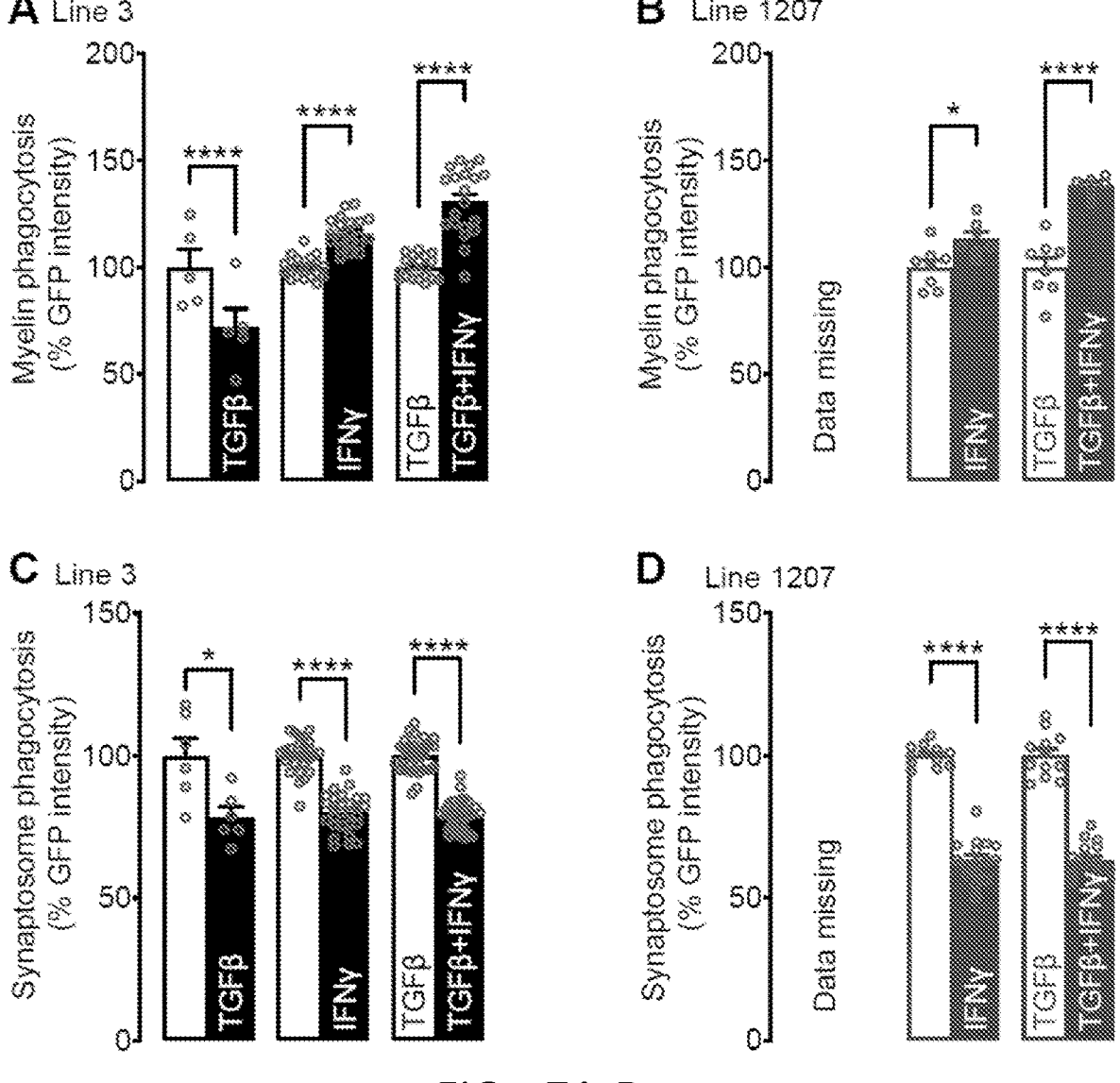
*FIGs. 7A-D*

REPROGRAMMING CELLS INTO HOMEOSTATIC MICROGLIA

CLAIM OF PRIORITY

This application is the U.S. National Phase Application under 35 U.S.C. § 371 of International Patent Application No. PCT/US2020/061637, filed on Nov. 20, 2020, which claims the benefit of U.S. Provisional Application Ser. No. 62/938,113, filed on Nov. 20, 2019. The entire contents of the foregoing are incorporated herein by reference.

FEDERALLY SPONSORED RESEARCH OR DEVELOPMENT

This invention was made with Government support under Grant Nos. NS088137; AG054672; and RG005092 awarded by the National Institutes of Health. The Government has certain rights in the invention.

TECHNICAL FIELD

Provided herein are methods for obtaining populations of reprogrammed M0-homeostatic tolerogenic microglial cells, and methods of use of these cells, e.g., for the treatment of neurodegenerative diseases associated with inflammation, e.g., Alzheimer's Disease (AD); Multiple Sclerosis (MS), e.g., progressive MS; and Amyotrophic Lateral Sclerosis (ALS).

BACKGROUND

Microglia and macrophages are the predominant inflammatory cells in Multiple Sclerosis (MS) lesions (Lucchinetti et al., Annals of neurology. 2000; 47(6):707-17), persisting in secondary-progressive MS (Prineas et al., Annals of neurology. 2001; 50(5):646-57), and microglial activation is believed to direct pro-inflammatory processes in almost all neurodegenerative diseases (Colonna and Butovsky, Annu. Rev. Immunol. 2017; 35, 441-468; Maleki and Mavest, Front Cell Neurosci. 2019 Jul. 31; 13:355). Despite advances in understanding of the pathophysiology of inflammatory neurodegeneration, there are few treatments for innate immune system-mediated diseases.

SUMMARY

Provided herein are methods for obtaining a population of reprogrammed M0-homeostatic tolerogenic microglial cells. The methods include providing an initial population of monocytes, e.g., peripheral blood monocytes (PBMC) from a subject; maintaining the PBMC in culture ex vivo in the presence of a sufficient amount of transforming growth factor-beta (TGFβ) and interferon-gamma (IFNγ) for a time and under conditions sufficient for the cells to become M0-homeostatic tolerogenic microglia.

In some embodiments, the initial population of PBMC comprise CD14+/CD16− PBMC. In some embodiments, the M0-homeostatic tolerogenic microglia are P2ry12+. In some embodiments, the M0-homeostatic tolerogenic microglia have increased expression of one or more homeostatic microglia genes and/or decreased expression of one or more MGnD genes as compared to the original CD14+/CD16− PBMC. In some embodiments, the one or more homeostatic microglia genes comprise Irf8, Math, and/or Mef2a. In some embodiments, the one or more MGnD genes comprise Spp1, Dab2, and/or Lgals1.

In some embodiments, the methods further include allowing the CD14+/CD16− PBMC to proliferate in culture, and/or allowing the reprogrammed M0 microglia to proliferate, to obtain a selected number of cells.

In some embodiments, the methods further include engineering the cells to reduce or eliminate expression of apolipoprotein E (APOE), e.g., using a CRISPR-Cas RNA-guided nuclease to induce a mutation that reduces or eliminates expression of APOE.

In some embodiments, the methods further include freezing one or more aliquots of the cells.

Also provided herein are methods for treating a subject who has a neurodegenerative disease associated with inflammation. The methods include providing a population of the reprogrammed M0-homeostatic tolerogenic microglial cells by the method of claim 1-9, wherein the initial population of monocytes are obtained from the subject, and administering a dose comprising a therapeutically effective amount of the cells reprogrammed M0-homeostatic tolerogenic microglial cells to the subject.

In some embodiments, the methods include administering a dose of the cells a plurality of times. In some embodiments, the methods include administering a dose of the cells once a week, twice a week, biweekly, monthly, bimonthly, every six weeks, every three months, every four months, every six months, every nine months, or once a year, for a plurality of doses.

In some embodiments, the dose of cells is administered by intravenous infusion.

In some embodiments, the neurodegenerative disease associated with inflammation is Alzheimer's Disease (AD); Multiple Sclerosis (MS), e.g., progressive MS; and Amyotrophic Lateral Sclerosis (ALS).

In some embodiments, the subject is a human.

Also provided herein are compositions comprising a population of reprogrammed M0-homeostatic tolerogenic microglial cells obtained by a method described herein, e.g., for use in a method of treating a subject who has a neurodegenerative disease associated with inflammation. In some embodiments, the methods include administering a dose of the cells a plurality of times. In some embodiments, the methods include administering a dose of the cells once a week, twice a week, biweekly, monthly, bimonthly, every six weeks, every three months, every four months, every six months, every nine months, or once a year, for a plurality of doses. In some embodiments, the cells are formulated to be administered by intravenous infusion. In some embodiments, the neurodegenerative disease associated with inflammation is Alzheimer's Disease (AD); Multiple Sclerosis (MS), e.g., progressive MS; and Amyotrophic Lateral Sclerosis (ALS). In some embodiments, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A-B. Loss of homeostatic microglial signature in human MS. A, P2RY12 immunohistochemistry in healthy and MS lesion. B, APOE qPCR analysis in MS tissue.

FIGS. 7A-E. The effect of TGFβ and IFNγ on phagocytosis of myelin and synaptosome in iMGLs. The mouse myelin and synaptosome phagocytosis in iMGLs treated with TGFβ only, IFNγ only, and combination of TGFβ+IFNγ on line 3 (A and C) and line 1207 (B and D). E) Phagocytosis of myelin and synaptosomes from both mouse and human in iMGLs treated with PBS or IFNγ. One-way ANOVA, *P<0.05, *P<0.001, **P<0.0001.

DETAILED DESCRIPTION

Figure 1:
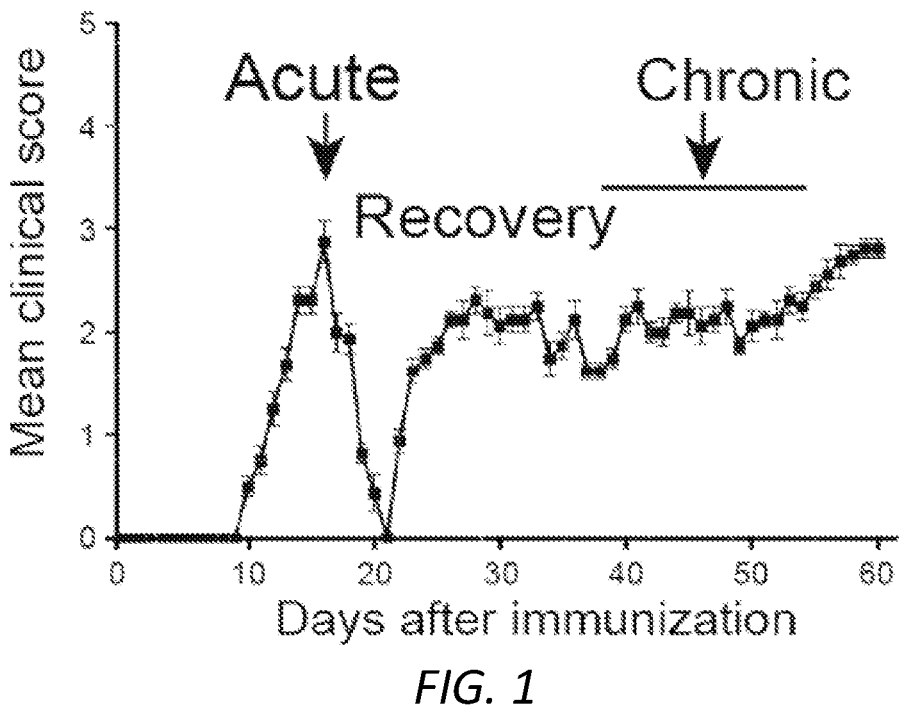
FIG. 1. Clinical scores of SJL-EAE mice (mean±s.e.m).

The major resident immune cells in the CNS are microglia. Microglia play an essential role in supporting normal CNS functions (Butovsky and Weiner, Nat Rev Neurosci. 2018 October; 19(10):622-635; Colonna and Butovsky, Annual review of immunology. 2017; 35:441-68), but these cells also strongly contribute to neuroinflammatory disorders (Prineas et al., Annals of neurology. 2001; 50(5):646-57; Strachan-Whaley et al., J Interferon Cytokine Res. 2014; 34(8):615-22; Ponomarev et al., J Neurosci Res. 2005; 81(3):374-89). Multiple sclerosis (MS) is a chronic inflammatory disease of the central nervous system (CNS) characterized by T cell and myeloid infiltrates leading to demyelination and loss of neurologic function (Sospedra and Martin, Annual review of immunology. 2005; 23:683-747). Despite some success treating relapsing MS, the progressive form of the disease is not well understood and there are minimal effective treatments for progressive MS. In contrast to relapsing MS, progressive forms of the disease may represent a local innate immune response that develops in the CNS following cell infiltration from the periphery (Jack et al., J Neurosci Res. 2005; 81(3):363-73; O'Loughlin et al., Cold Spring Harb Perspect Med. 2018; 8(2); Baufeld et al., J Neural Transm (Vienna). 2018; 125(5):809-26; Croxford et al., Immunity. 2015; 43(3):502-14; Lassmann et al., Nat Rev Neurol. 2012; 8(11):647-56). Monocyte recruitment may trigger disease progression in experimental autoimmune encephalomyelitis (EAE) (an animal model of MS; see Ajami et al., Nature neuroscience. 2018; 21(4):541-51; Yamasaki et al., The Journal of experimental medicine. J Exp Med. 2014 Jul. 28; 211(8):1533-49; Ajami et al., Nature neuroscience. 2011; 14(9):1142-9) and blocking their CNS entry suppresses EAE (Ajami et al., 2011). In MS, the therapeutic natalizumab for relapsing-remitting MS prevents leukocyte entry into the CNS (Steinman, J Cell Biol. 2012; 199(3):413-6; Yednock et al., Nature. 1992; 356(6364):63-6; Sanford, Drugs. 2014; 74(12):1411-33). It has been proposed that microglia arise from Ly6C$^H$VCCR2$^+$ monocytes in EAE (Mildner et al., Nature neuroscience. 2007; 10(12):1544-53), however, this concept has been debated. Several studies showed that microglial function is not replaceable by peripheral monocytes (Butovsky et al., Nature neuroscience. 2014; 17(1):131-43; Ajami et al., 2011; Ajami et al., Nature neuroscience. 2007; 10(12):1538-43; Bruttger et al., Immunity. 2015; 43(1):92-106). Conversely, other studies showed that peripheral monocytes can infiltrate and engraft long-term into the CNS after microglial depletion and, to some extent, upregulate microglial genes (Cronk et al., The Journal of experimental medicine. 2018; 215(6):1627-47; Bennett et al., Neuron. 2018; 98(6):1170-83 e8).

We have recently identified a unique TGFβ-dependent molecular signature of homeostatic microglia (M0) and developed robust tools to investigate its biology (Butovsky et al., Nature neuroscience. 2014; 17(1):131-43). Further, Apolipoprotein E (APOE) signaling regulates the microglia neurodegenerative (MGnD) phenotype in EAE (Butovsky et al., Annals of neurology. 2015; 77(1):75-99). APOE also plays an important role in cholesterol and lipid homeostasis and accelerates Aβ aggregation in Alzheimer's Disease (AD) (Liao et al., J Neurosci. 2014; 34(21):7281-92; Holtzman et al., Cold Spring Harb Perspect Med. 2012; 2(3): a006312). The APOE c4 allele is a major risk factor in AD (Castellano et al., Sci Transl Med. 2011; 3(89):89ra57; Verghese et al., Proc Natl Acad Sci U S A. 2013; 110(19): E1807-16). APOE has been hypothesized to play a role in MS, but studies to date have yielded inconclusive results (Lill et al., J Med Genet. 2012; 49(9):558-62). We recently identified a novel role of APOE as a master regulator of inflammatory microglia in neurodegeneration (Krasemann et al., Immunity. 2017; 47(3):566-81 e9). Furthermore, genetic ablation of Apoe ameliorates EAE (Shin et al., Journal of neuroimmunology. 2014; 271(1-2):8-17). During the course of EAE, microglia lose their homeostatic signature and acquire an MGnD phenotype. Mutually antagonistic pathways, driven by TGF0 and APOE signaling in microglia, dictate a phenoconversion between M0 and MGnD phenotypes (Krasemann et al., 2017).

Figure 5:
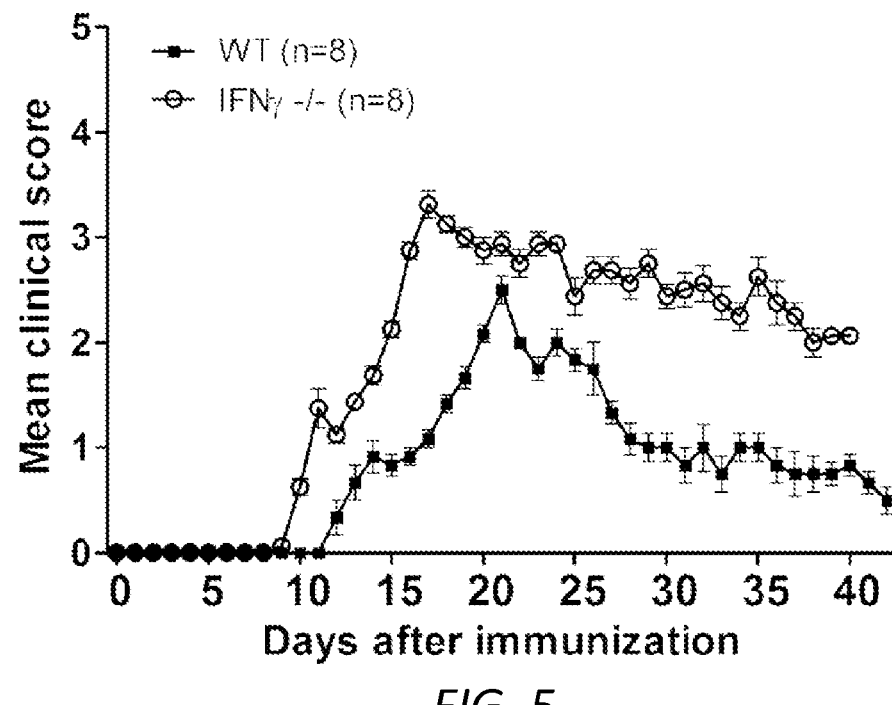
FIG. 5. Disease score in WT vs. Ifng$^{-/-}$ EAE mice.
Figures 6A, 6B:
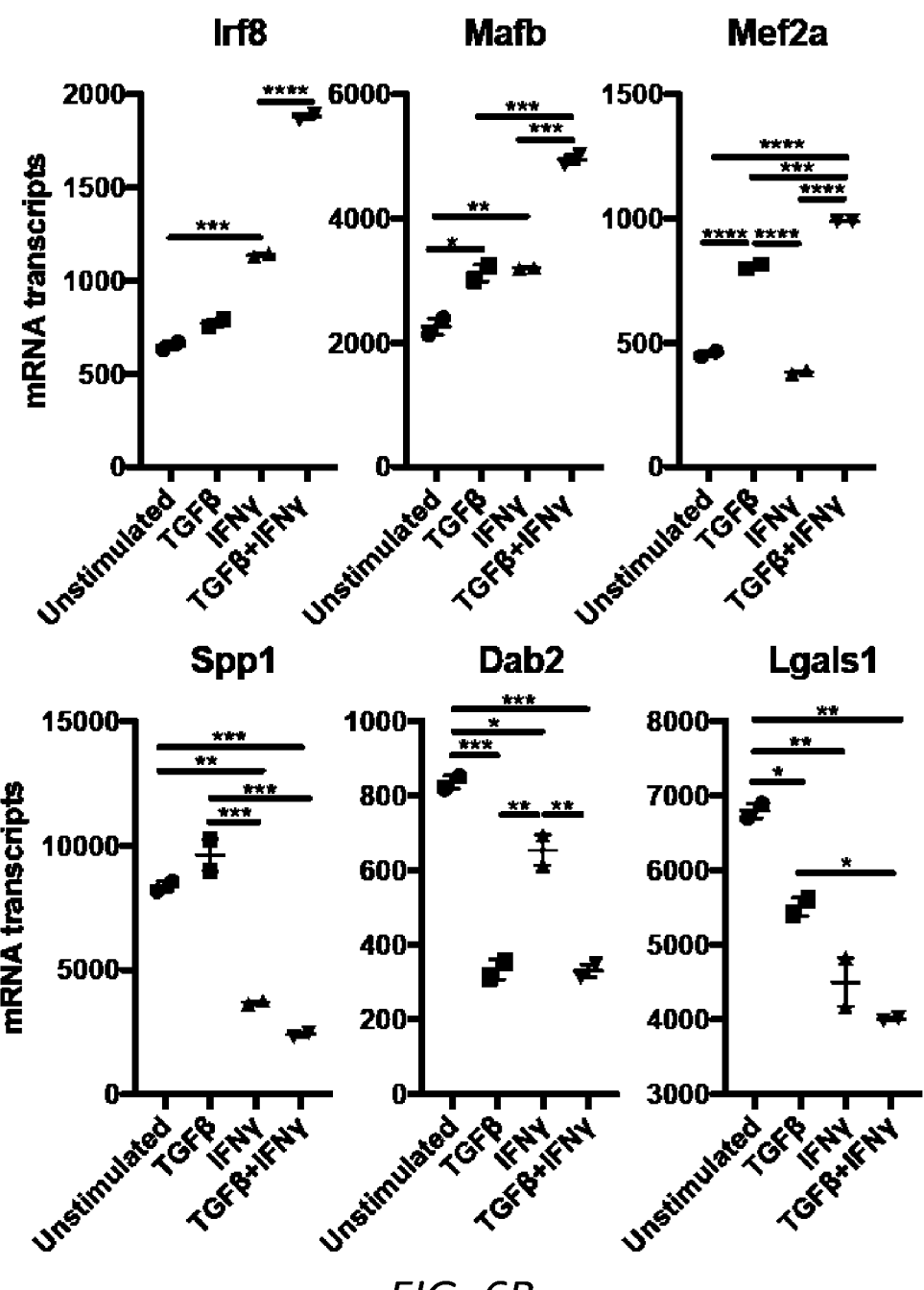
FIG. 6A-B. TGFβ-IFNγ signaling induces M0 signature in peripheral monocytes. A, Selected synergistically effected homeostatic genes. B, Selected MGnD genes effected by TGFβ+IFNγ signaling. *P<0.05, P<0.01, *P<0.001 (one-way ANOVA).

Reprogramming Patient-Derived Monocytes into Homeostatic MG-Like Cells Via APOE-TGFβ/IFNγ Pathway As noted above, inflammatory monocytes play a central and complex role in disease progression in mouse models of EAE and in progressive MS. In secondary progressive MS, where there are minimal effective treatments, monocyte-mediated inflammation may contribute to disease progressionξ. During neuroinflammation in EAE, Ly6C$^{Hi}$ monocytes are recruited to the CNS via a CCR2-dependent process (Mildner et al., 2007; Lu et al., FASEB J. 2011; 25(1):358-69; Mildner et al., J Immunol. 2008; 181(4):2713-22; Mildner et al., Brain: a journal of neurology. 2009;

132(Pt 9):2487-500). The loss of TGFβ signaling in recruited macrophages leads to demyelination and fatal motor disease (Lund et al., Nature immunology. 2018; 19(5):1-7). Furthermore, mice deficient in TGFβ in the CNS rapidly worsen and die upon induction of EAE (FIG. 10). Additionally, loss of TGFβ signaling and the homeostatic transcriptional program directly correlates with EAE disease progression (FIG. 2). Importantly, we found that Ifnγ⁻/⁻ mice lack homeostatic microglia at the recovery stage in EAE (FIG. 5). Treatment of peripheral monocytes with TGFβ and IFNγ induced the microglia homeostatic signature including the TFs Mafb, Mef2a, Irf8 and suppressed APOE pathways (FIG. 6). Furthermore, reprogrammed cells, whether from iPSC-derived iMGLs or human adult PBMC, increased myelin and synaptosome phagocytosis. Based on these findings, provided herein are methods that induce TGFβ/IFNγ signaling to reprogram inflammatory or peripheral monocytes into homeostatic-tolerogenic MG-like cells, which in turn can be administered to contribute to resolution of inflammation and reduction of symptoms of inflammatory neurodegenerative diseases, including the uptake of myelin and promotion of remyelination.

Reprogramming Human CD14⁺/CD16⁻ Monocytes with APOE ε2, ε3 and ε4 Variants into M0-Homeostatic Microglia in MS Patients.

There is a gain of pro-inflammatory phenotype in 'classical' CD14⁺/CD16⁻ monocytes along the progression of MS (Butovsky et al., The Journal of clinical investigation. 2012; 122(9):3063-87). As noted above, IFNγ signaling was crucial for M0-microglia restoration in EAE associated with recovery (Example 4, FIG. 5) and treatment of both mouse and human 'classical' monocytes with TGFβ+IFNγ induced the M0-microglia signature including the transcription factors Mafb, Mef2a, Irf8 and suppresses APOE pathways (Example 5).

Figures 9A, 9B:
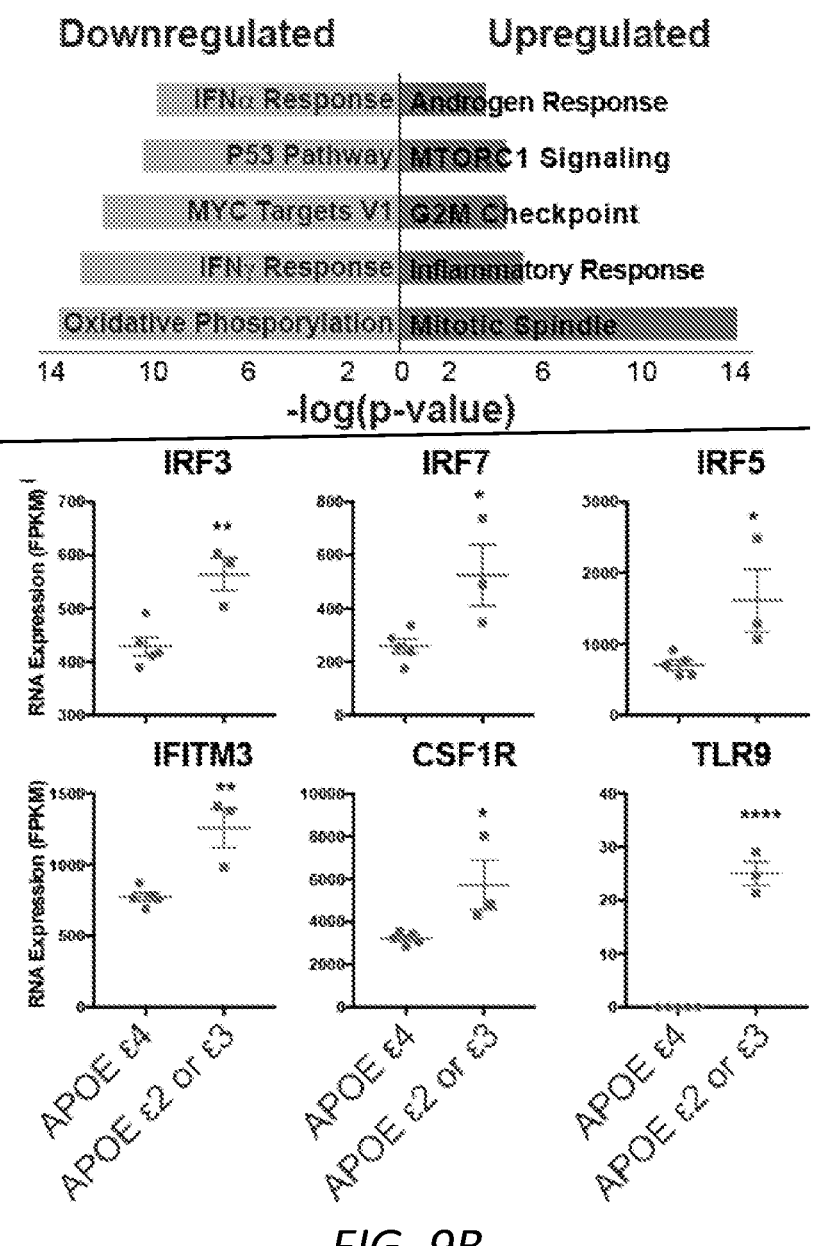
FIGS. 9A-B. IFNγ signaling is suppressed in classical CD14$^+$/CD16$^-$ monocytes from APOE ε4 carriers. A, Gene set enrichment analysis showing suppressed pathways (left) and upregulated pathways (right) in healthy donors carrying at least one APOE ε4 allele. B, Selected differentially expressed genes between APOE ε4 vs. APOE ε2 and 3 carriers. *P<0.05, P<0.01, *P<0.001 (t-test).

Further, monocytes from APOE ε4 carriers had suppressed IFNγ signaling (FIGS. 9A-B). Importantly, APOE ε4 induced a pro-inflammatory phenotype in MG-like cells derived from human isogenic iPSCs (Lin et al., Neuron. 2018; 98(6):1294). Although APOE has not been implicated in MS susceptibility (Lill et al., J Med Genet. 2012; 49(9): 558-62), it is currently unclear if a particular APOE variant is involved in disease type, course, or severity, and studies have reported that the APOE ε4 variant associates with progressive forms of MS (Cocco et al., Neurology. 2005; 64(3):564-6; Losonczi et al., Swiss Med Wkly. 2010; 140: w13119). Based on these findings, reprogramming of CD14⁺/CD16⁻ monocytes from progressive forms of MS into MG-like cells may be impaired, particularly in subjects with APOE ε4 alleles. Thus, in some embodiments the methods include silencing APOE to promote reprogramming of these cells to homeostatic MG-like cells, which can be used in therapeutic applications described herein.

The methods can include determining the subject's APOE genotype, using known methods. The 3 major isoforms of human apolipoprotein E (apoE2, –E3, and –E4) are coded for by 3 alleles (epsilon 2, 3, and 4). The E2, E3 (107741.0015), and E4 (107741.0016) isoforms differ in amino acid sequence at 2 sites, residue 112 and residue 158. At residues 112/158, apoE2, –E3, and –E4 have Cys/Cys, Cys/Arg, and Arg/Arg, respectively (Weisgraber et al., J. Biol. Chem. 256: 9077-9083, 1981; Rall et al., Proc. Nat. Acad. Sci. 79: 4696-4700, 1982; Smit et al. J. Lipid Res. 31: 45-53, 1990). E3 (Cys112/Arg158) is the most frequent (often considered the wildtype) isoform. Four different mutations giving a band at the E2 position with isoelectric focusing have been described: E2(arg158-to-cys), E2(lys146-to-gln), E2(arg145-to-cys) and E2-Christchurch (arg136-to-ser). E2(arg158-to-cys) is the most common of the four E2 alleles.

A number of methods are known in the art for reducing APOE expression. In some embodiments, the methods include using gene editing, e.g., CRISPR-Cas9 gene editing, to introduce a deletion or mutation that abrogates expression of APOE. In some embodiments, the methods include determining whether a subject has an APOE e4 allele, and deleting or reducing expression from the APOE ε4 allele.

Methods of Treatment

Provided herein are methods of reducing neuroinflammation in a subject and for treating neurodegenerative diseases associated with inflammation, including Alzheimer's Disease (AD); Multiple Sclerosis (MS), e.g., progressive MS; and Amyotrophic Lateral Sclerosis (ALS). The present methods can be used for any mammalian subject, e.g., human or non-human subjects, e.g., veterinary subjects including primates, cats, dogs, horses, goats, sheep, cows, and so on. The methods include obtaining monocytes, e.g., peripheral blood monocytes (PBMC), e.g., CD14+/CD16– PBMC, from a subject (See, e.g., Butovsky et al., J Clin Invest. 2012 September; 122(9):3063-87). The obtained PBMC are then reprogrammed by being maintained in culture ex vivo in the presence of TGFβ (e.g., about 20-100 ng/ml, e.g., 50 ng/ml)+IFNγ (e.g., about 10-50 ng/ml, e.g., 25 ng/ml) for 3-7 days, e.g., 5 days, a time and sufficient for the cells to become P2ry12+M0-homeostatic tolerogenic microglia. The cells have increased expression of homeostatic microglia genes including the Transcription Factors (TFs) Irf8, Mafb, and Mef2a (FIG. 6A) and decrease MGnD genes including Spp1, Dab2, and Lgals1 (FIG. 6B) as compared to the original CD14+/CD16– PBMC. The CD14+/CD16– PBMC can be proliferated prior to reprogramming, or the reprogrammed M0 microglia can be proliferated, to obtain a sufficient number of cells for use in treatment. In some embodiments, the methods include freezing one or more aliquots of the cells for future use.

Once the reprogrammed M0-homeostatic tolerogenic microglial cells have been obtained, the methods can include re-administering a sufficient dose (e.g., a therapeutically effective amount) of the cells to the subject from whom the original population of PBMC was obtained, e.g., by intravenous infusion. In some embodiments, 1-20×10*6 cells/kg are administered. See, e.g., T-regulatory Cells in ALS (Tregs in ALS); ClinicalTrials.gov Identifier: NCT04055623, available at clinicaltrials.govict2/show/NCT04055623. The methods can include administering a sufficient dose of the cells a plurality of times, e.g., once a week, twice a week, biweekly, monthly, bimonthly, every six weeks, every three months, every four months, every six months, every nine months, or once a year, for a plurality of doses. As used herein, a therapeutically effective amount is an amount to ameliorate one or more symptoms of the neuroinflammation or disease, e.g., to improve or to stop or slow decline in one or more cognitive, neurological, or motor functions in the subject. For example, symptoms of MS can include sensory loss, visual disturbance, double vision, muscle weakness, ataxia and impaired balance. See, e.g., Huang et al., Exp Ther Med. 2017 June; 13(6): 3163-3166; Loma and Heyman, Curr Neuropharmacol. 2011 September; 9(3): 409-416.

Compositions

Also provided herein are compositions comprising reprogrammed M0-homeostatic tolerogenic microglial cells obtained using a method described herein, optionally wherein the cells have been engineered to lack one or more APOE alleles.

EXAMPLES

The invention is further described in the following examples, which do not limit the scope of the invention described in the claims.

Figure 2A:
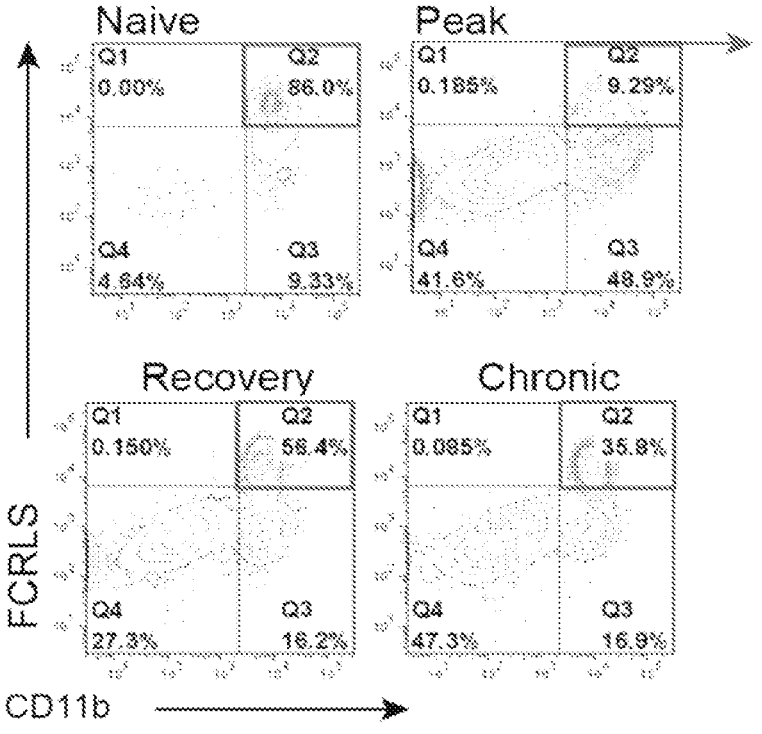
FIGS. 2A-B. Loss of homeostatic microglial signature in EAE mice. A, Representative FACS plots of FCRLS+/CD11b+ microglia and gating strategy to isolate resident FCRLS+ microglia (Q2) from recruited myeloid cells (Q3). B, e, Apoe expression correlated with disease score.
Figure 2B:
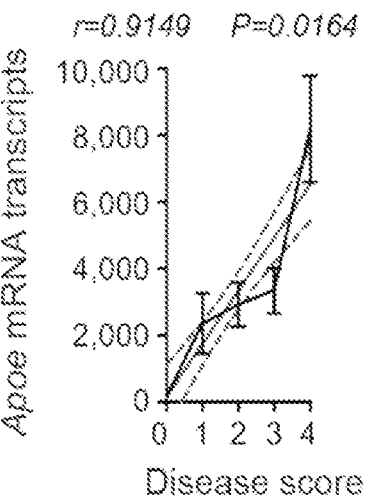

Example 1. Induction of APOE and Suppression of TGFβ Signaling Leads to Loss of M0-Homeostatic Tolerogenic Microglia and Induction of MGnD-Neurodegenerative Microglia Associated with EAE Progression We recently identified a molecular signature of FCRLS⁺ microglia in different disease stages of multiple EAE mouse models (Krasemann et al., 2017) (FIG. 1). In order to distinguish resident microglia from recruited myeloid cells, we isolated FCRLS+microglia from the spinal cord of EAE mice at different stages (FIG. 2A). Of note, FCRLS is not suppressed in MGnD-microglia and thus can be used to isolate M0- and MGnD-microglia (Krasemann et al., 2017). Nanostring MG550 analysis showed suppression of 248 homeostatic genes during acute and chronic disease stages including key microglial homeostatic genes such as P2ry12, Tmem119, Gpr34, June, Olfml3, Csflr, Hexb, Mertk, Rhob, Cx3Crl, Tgfbr1 and Tgfß1 and the upregulation of inflammatory molecules including Spp1, Itgax, Ax1, Lilrb4, Clec7a, Tlr2, Ccl2, Csfl and Apoe, which was among the most upregulated genes. We confirmed downregulation of homeostatic microglial molecules including P2RY12 (Butovsky et al., 2014) at the protein level at the peak stage. Importantly, Apoe expression in microglia correlated with disease score in EAE (FIG. 2B). In collaboration with Dr. Hans Lassmann, we analyzed MS lesions with different markers for microglial functional states. We found P2RY12 loss in active MS lesions (FIG. 3A) was associated with increased APOE expression (FIG. 3B and Zrzavy et al., Brain: a journal of neurology. 2017; 140 (7): 1900-13). We tested the tolerogenic ability of microglia isolated at EAE peak to inhibit T cell proliferation in vitro (Bai et al., PLOS One. 2009; 4(11):e7869). CFSE-labeled T cells were stimulated in vitro with anti-CD3/CD28 in the presence of WT spinal cord microglia. We found that M0-homeostatic microglia isolated from naïve WT mice suppressed T cell proliferation (Krasemann et al., 2017) while microglia isolated from the spinal cord during acute phase in EAE do not (Krasemann et al., 2017). Importantly, Apoe⁻/⁻ microglia, isolated at the peak of EAE, suppressed T cell proliferation (Krasemann et al., 2017). These results demonstrate that APOE inhibits the homeostatic-tolerogenic function of microglia, which may be responsible for microglial dysfunction in MS.

Example 2. The Role of TGFβ-APOE Signaling in Microglia Phenotype Switch in Disease We demonstrated a critical role for TGFβ signaling in the maintenance homeostatic M0-microglia (Butovsky et al., 2014). TGFβ signaling activates SMAD proteins, which in turn induce microglia homeostatic genes including P2ry12, Tgfbr1, Tmem119, Fcr1s, Cx3cr1, Sall and Egr1 (Butovsky et al., 2014; Gosselin et al., Cell. 2014; 159(6):1327-40). Loss of TGFβ signaling in microglia is associated with loss of the M0-homeostatic phenotype and development of severe paralysis (Butovsky et al., 2014; Lund et al., Nature immunology. 2018; 19(5):1-7). These microglia highly express MGnD-microglial genes including Apoe, Ax1, and Dab2 and suppress major homeostatic regulators and molecules including Egr1, Sal1, P2ry12, Tmem119, and Hexb (Butovsky et al., 2014; Lund et al., Nature immunology. 2018; 19(5):1-7). Recently, two independent groups confirmed that a lack of CNS TGFβ signaling lead to the development of the MGnD phenotype, neurological abnormalities and death (Wong et al., Nature immunology. 2017; 18(6):633-41; Qin et al., Cell. 2018; 174(1):156-71 e16). We stereotaxically injected apoptotic neurons or oligodendrocytes into WT mouse brains and profiled the transcriptome of phagocytic vs. non-phagocytic microglia (Krasemann et al., 2017). We observed a switch from M0- to MGnD-phenotype associated with the induction of Apoe and the suppression of microglia homeostatic signature. Independent studies have shown an increase of Apoe and a decrease of homeostatic microglial genes in neuroinflammation (Keren-Shaul et al., Cell. 2017; 169(7):1276-90 e17; Mathys et al., Cell reports. 2017; 21(2):366-80). Importantly, as shown in FIG. 3B, APOE expression was induced in acute MS lesions, a finding confirmed by the Stevens lab (Hammond et al., bioRxiv 406140; doi.org/10.1101/406140). Genetic ablation of Apoe significantly affected 1,249 genes in phagocytic microglia. Among 68 genes commonly suppressed in disease, 19 genes were restored in Apoe⁻/⁻ microglia including P2ry12, Tgfbr1, Egr1, Mef2a, and Spi 1 (PU.1), a lineage-determining TF for myeloid cells. In addition, APOE induced expression of Bh1he40, which is essential for pathogenicity in neuroinflammation (Lin et al., Nat Commun. 2014; 5:3551; Sun et al., Nature immunology. 2001; 2(11):1040-7) and Spp1, which is involved in inflammatory and degenerative processes (Carecchio and Comi, J Alzheimers Dis. 2011; 25(2):179-85). These findings identify the suppression of TGFβ and upregulation of APOE signaling as the major pro-inflammatory regulatory pathway in microglia in neuroinflammation and provide the basis for investigating the mechanism of microglia dysfunction mediated by the TGFβ-APOE pathway in EAE.

Figure 4:
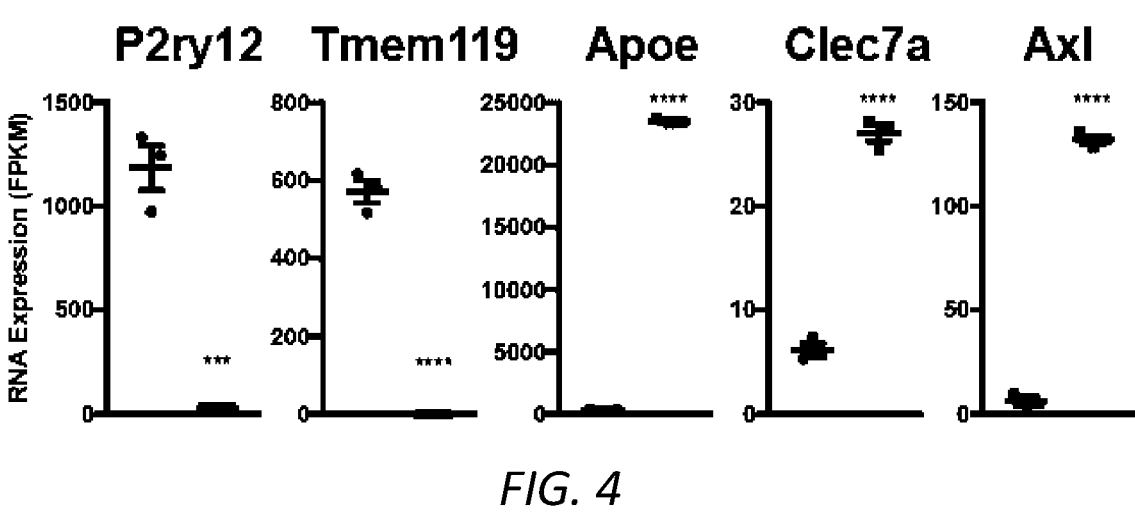
FIG. 4. Homeostatic transcriptome profiles in sorted CD11b+/CD45+ microglia from Tgfbr2$^{fl/fl}$ and Cx3cr1-Cre$^{ERT2/+}$:Tgfbr2$^{fl/fl}$ mice.

Example 3. TGFβ is a Negative Regulator of APOE Signaling in Microglia, and Loss of TGFβ Signaling in Recruited Macrophages Leads to Demyelination and Fatal Motor Disease Microglial transcriptional profiling demonstrated downregulation of TGFβ-dependent genes including P2ry12 and Tmem119 and the induction of MGnD genes including Clec7a, Ax1 and Apoe (FIG. 4). Importantly, we observed progressive deterioration in muscle strength in four-paw hanging-wire tests starting in the fourth week after Tgfbr2 deletion and motor impairments by six weeks (Lund et al., Nature immunology. 2018; 19(5):1-7). These observations confirm a crucial role for TGFβ signaling in the maintenance of homeostatic microglia.

To investigate the role of TGFβ signaling in macrophages recruited to the CNS, we generated bone marrow chimeras using Cx3cr1-Cre$^{ER/+}$:Tgfbr2$^{fl/fl}$ donor cells transferred into Cx3cr1-Cre$^{ER/+}$:R26$^{DTA/+}$ mice such that TAM administration depleted microglia and deleted Tgfbr2 in CX3CR1⁺ recruited macrophages. These chimeras developed severe motor impairments with most mice reaching the ethical endpoint by day 40 (Lund et al., 2018). We observed an accumulation of lesions along the entire spinal cord that were predominantly located in the dorsal and lateral columns of the cervical spinal cord (Lund et al., 2018). Transcriptomic analysis of recruited macrophages with and without Tgfbr2 revealed an enrichment of MGnD genes and a downregulation of genes associated with the homeostatic M0-microglia signature as well as IRF8, a critical TF in microglia development (Kierdorf et al., Nature neuroscience. 2013; 16(3):273-80) and an MS susceptibility locus (Masuda et al., Purinergic Signal. 2014; 10(3):515-21). These data suggest that TGFβ signaling in monocyte-derived CNS macrophages is essential to prevent the onset of fatal motor disease and may facilitate the phenotypic Ly6C$^{Hi}$Imonocyte to MG-like cell switch.

Example 4. IFNγ Signaling Regulates Homeostatic Microglia

MS and EAE are T cell-driven autoimmune diseases of the CNS (Baxter, Nat Rev Immunol. 2007; 7(11):904-12). Initially, it was believed that IFNγ, a hallmark cytokine of Th1 cells, played a pathogenic role in EAE, based on a positive correlation between IFNγ levels and EAE severity (Baxter, Nat Rev Immunol. 2007; 7(11):904-12; Olsson, Neurology. 1995; 45(6 Suppl 6):S11-5). However, Ifny$^{-/-}$ and Ifngrl$^{-/-}$ mice developed more severe disease (Baxter, 2007; Ferber et al., J Immunol. 1996; 156(1):5-7; Willenborg et al., J Immunol. 1996; 157(8):3223-7). Importantly, blocking IFNγ signaling in CNS resident cells enhanced disease severity (FIG. 5) (Willenborg et al., 1996). Therefore, investigating IFNγ signaling in microglia is crucial for understanding the mechanism underlying the development of MS/EAE. We found that during recovery stage, P2ry12$^+$ homeostatic microglia recovered in WT mice, but not in Ifny$^{-/-}$ mice. These results identify IFNγ signaling as a positive regulator of homeostatic microglia replenishment in EAE.

Example 5. Reprograming Peripheral Monocytes into M0-Microglia Via TGFβ-IFNγ Signaling We observed the loss of homeostatic microglia in the spinal cord of Ifny$^{-/-}$ mice at the recovery stage of EAE (Example 4, FIG. 5). Interestingly, we did not find Iba1$^+$/P2ry12$^-$ cells at this stage in WT mice. Iba1 is expressed in both microglia and recruited myeloid cells, therefore we postulated that recruited monocytes acquire the homeostatic microglia signature in an IFNγ-dependent manner. TGFβ+IFNγ treatment of mouse bone marrow-derived macrophages (BMDM) and human blood CD14$^+$/CD16$^-$ monocytes induced microglia homeostatic signature genes and suppressed APOE pathways. We performed an independent experiment on mouse BMDMs to identify synergistic effects of combinatorial signaling. We found that TGFβ+IFNγ increased homeostatic microglia genes including the TFs Irf8, Mafb, and Mef2a (FIG. 6, top) and decreased MGnD genes including Spp1, Dab2, and Lgals1 (FIG. 6, bottom). Without wishing to be bound by theory, it was hypothesized that TGFβ/IFNγ signaling reprogrammed mouse inflammatory Ly6C$^{Hi}$ and human CD14$^+$/CD16$^-$ monocytes into homeostatic MG-like cells, contributing to the resolution of EAE.

Figure 7E:
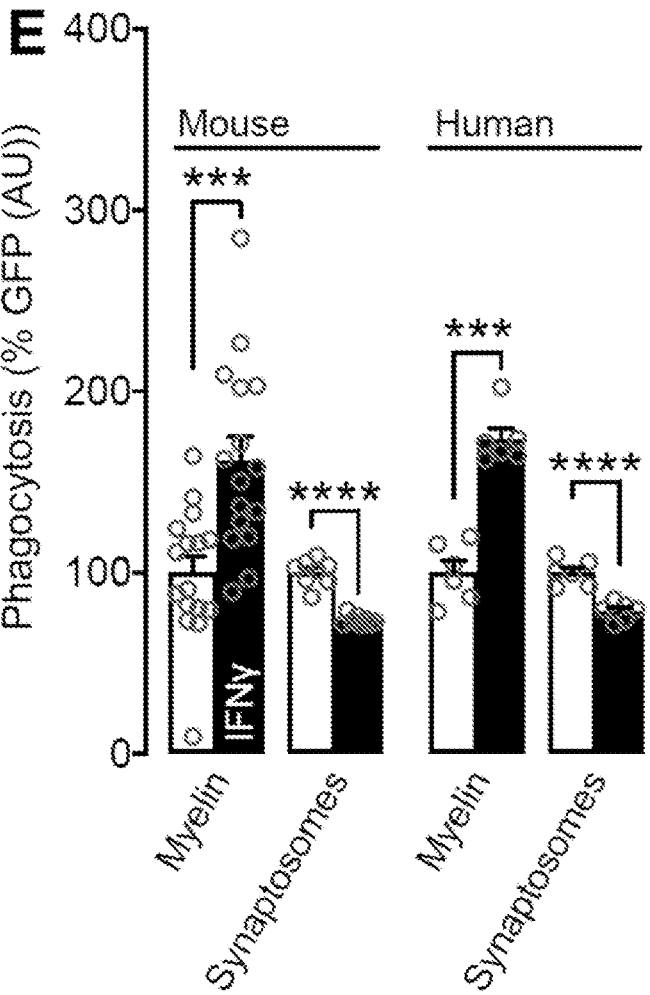

Example 6. Reprogramming iPSC-Derived Human Microglia (iMGLs) into M0-Homeostatic Microglia with Increased Myelin Phagocytosis We generated iPSC-derived human microglia (iMGLs) from iPSC lines 3 and 1207 following an established protocol (Abud et al., Neuron. 2017, 94(2):278-93 e91; Mancuso et al., Nat Neurosci 22, 2111-2116). The iMGLs were treated with TGFβ only, IFNγ only, and a combination of TGFβ+IFNγ as above. RNAseq analysis showed that combinatorial effect of TGFβ+IFNγ induced expression of HLA-related genes in both line 3 and line 1207, including HLA-DRB1, HLA-DPA1, HLA-DPB1. Importantly, we found that while TGFβ reduced myelin uptake, IFNγ alone as well as combinatorial treatment with TGFβ+IFNγ increased myelin uptake, as measured using pHrodo-labelled mouse myelin7 (FIG. 7A, B). Conversely, when studying uptake of synaptosomes from mouse brain8, no effect was seen after TGFβ application and a reduction was observed after application of IFNγ with or without TGFβ (FIG. 7C, D). We confirmed the effect of IFNγ on human myelin and synaptosomes (FIG. 7E).

Figure 8:
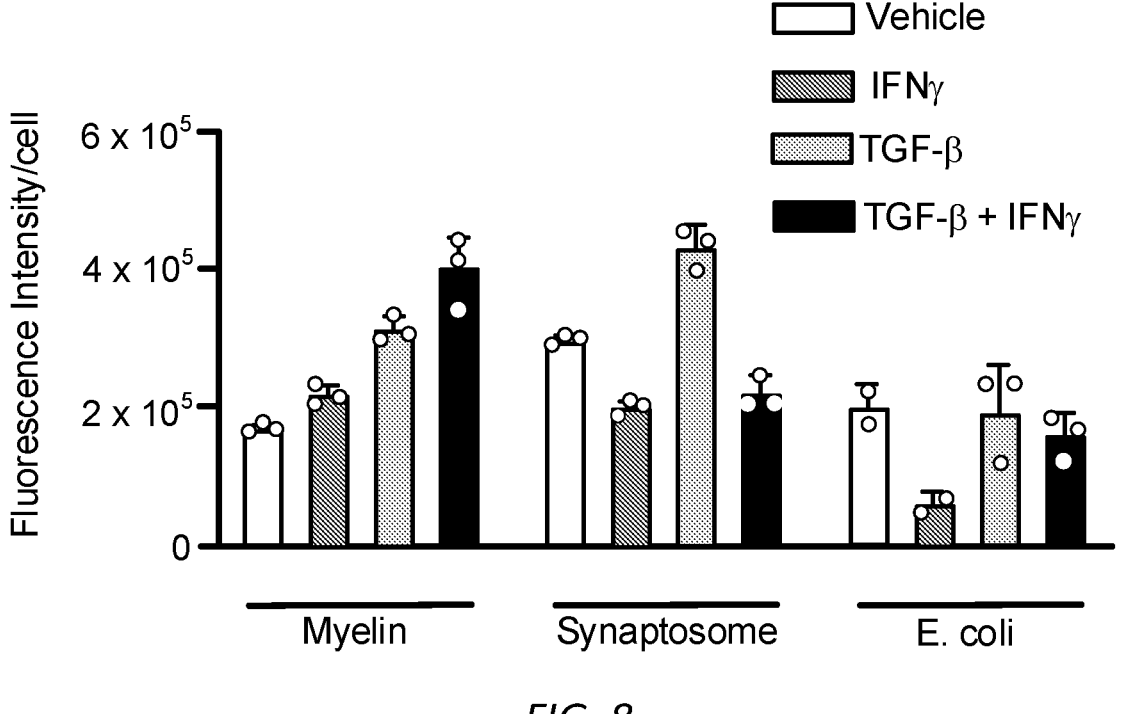
FIG. 8. The combinatorial effect of TGFβ and IFNγ on phagocytosis of myelin and synaptosome in adult human microglia. The human myelin and synaptosome, *E. coli* particles phagocytosis in adult human microglia treated with TGFβ only, IFNγ only, and combination of TGFβ+IFNγ at 3 hrs timepoint. Fluorescence intensity normalized to cell numbers was measured by FACS. Dots represent technical replicates.

Example 7. Combinatorial Treatment with TGFβ and IFNγ Increase Phagocytosis of Myelin and Synaptosomes by Adult Human Microglia Adult human microglia were treated with TGFβ only, IFNγ only, and combination of TGFβ+IFNγ for 2 days. Fluorescence intensity normalized to cell numbers showed that combinatorial treatment with TGFβ+IFNγ increased myelin uptake (FIG. 8). In contrast, there was a reduction of synaptosome uptake in the combination of TGFβ+IFNγ, compared to TGFβ alone (FIG. 8). When the cells were treated with E. coli., there were no significant changes in the groups between TGFβ+IFNγ and TGFβ alone (FIG. 8). These results support our original hypothesis that IFNg signaling enhances beneficial microglia phenotype which may facilitate in recovery phases in MS.

Example 8. IFNγ Signaling was Suppressed in Classical CD14$^+$/CD16$^-$ Monocytes (Ly6C$^{Hi}$ Analogues) from APOE ε4 Carriers Although APOE has not been implicated in MS susceptibility (Lill et al., 2012), it is unknown if APOE variant is involved in disease type, course, or severity, and studies have reported that APOE ε4 associates with progressive forms of MS (Cocco et al., Neurology. 2005; 64(3):564-6; Losonczi et al., Swiss Med Wkly. 2010; 140:w13119). We isolated classical inflammatory monocytes from whole blood of healthy donors carrying APOE ε2, ε3 and ε4 alleles and sequenced their transcriptomes. Gene set enrichment analysis (GSEA) demonstrated that monocytes from donors carrying at least one APOE ε4 allele had suppressed IFNγ signaling relative to donors carrying only APOE ε3 and ε2 alleles (FIG. 9A). A number of interferon-induced genes were suppressed in APOE ε4 carriers including IRF3, IRF7, and IRF5 (FIG. 9B), which has been identified as a MS susceptibility locus (Kristjansdottir et al., J Med Genet. 2008; 45(6):362-9; Tang et al., Genet Mol Res. 2014; 13(2):4473-85). These results suggest that the APOE ε4 allele inhibits IFNγ signaling in inflammatory CD14$^+$/CD16$^-$ monocytes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has a neurodegenerative disease associated with inflammation, the method comprising:

providing a population of reprogrammed M0-homeostatic tolerogenic microglial cells by a method comprising:

providing an initial population of peripheral blood monocytes (PBMC) from the subject who has a neurodegenerative disease associated with inflammation;

maintaining the PBMC in culture ex vivo in the presence of a sufficient amount of transforming growth factor-beta (TGFβ) and interferon-gamma (IFNγ) for a time and under conditions sufficient for the PBMC to become M0-homeostatic tolerogenic microglia cells, and administering a dose comprising a therapeutically effective amount of the reprogrammed M0-homeostatic tolerogenic microglial cells to the subject.

2. The method of claim 1, comprising administering a dose of the M0-homeostatic tolerogenic microglial cells a plurality of times.

3. The method of claim 2, comprising administering a dose of the M0-homeostatic tolerogenic microglial cells once a week, twice a week, biweekly, monthly, bimonthly, every six weeks, every three months, every four months, every six months, every nine months, or once a year, for a plurality of doses.

4. The method of claim 1, wherein the dose of the M0-homeostatic tolerogenic microglial cells is administered by intravenous infusion.

5. The method of claim 1, wherein the neurodegenerative disease associated with inflammation is Alzheimer's Disease (AD); Multiple Sclerosis (MS); or Amyotrophic Lateral Sclerosis (ALS).

6. The method of claim 1, wherein the subject is a human.

7. The method of claim 1, wherein the initial population of PBMC comprise CD14+/CD16– PBMC.

8. The method of claim 1, wherein the M0-homeostatic tolerogenic microglial cells are P2ryl2+.

9. The method of claim 1, wherein the M0-homeostatic tolerogenic microglial cells have increased expression of one or more homeostatic microglia genes and/or decreased expression of one or more MGnD genes as compared to the original CD14+/CD16– PBMC.

10. The method of claim 9, wherein the one or more homeostatic microglia genes comprise Irf8, Mafb, and/or Mef2a.

11. The method of claim 9, wherein the one or more MGnD genes comprise Spp1, Dab2, and/or Lgals1.

12. The method of claim 7, further comprising allowing the CD14+/CD16– PBMC to proliferate in culture, and/or allowing the reprogrammed M0-homeostatic microglia microglial cells to proliferate, to obtain a selected number of cells.

13. The method of claim 1, further comprising engineering the reprogrammed M0-homeostatic microglial cells to reduce or eliminate expression of apolipoprotein E (APOE).

14. The method of claim 13, comprising using a CRISPR-Cas RNA-guided nuclease to induce a mutation that reduces or eliminates expression of APOE.

15. The method of claim 1, further comprising freezing one or more aliquots of the reprogrammed M0-homeostatic microglial cells.

* * * * *